(12) United States Patent
Aoki et al.

(10) Patent No.: US 7,776,881 B2
(45) Date of Patent: *Aug. 17, 2010

(54) HYPERLIPEMIA THERAPEUTIC AGENT

(75) Inventors: Taro Aoki, Tokorozawa (JP); Junji Yamaguchi, Higashimurayama (JP); Yusuke Sasaki, Higashimurayama (JP)

(73) Assignees: Kowa Co., Ltd., Nagoya-shi (JP); Nissan Chemical Industries, Ltd., Tokyo (JP)

( * ) Notice: Subject to any disclaimer, the term of this patent is extended or adjusted under 35 U.S.C. 154(b) by 643 days.

This patent is subject to a terminal disclaimer.

(21) Appl. No.: 11/293,217

(22) Filed: Dec. 5, 2005

(65) Prior Publication Data

US 2006/0111437 A1 May 25, 2006

Related U.S. Application Data

(63) Continuation of application No. 10/780,640, filed on Feb. 19, 2004, now Pat. No. 7,022,713.

(51) Int. Cl.
*A61K 31/47* (2006.01)
*A61K 31/22* (2006.01)
*A61K 31/20* (2006.01)

(52) U.S. Cl. .................. 514/311; 514/549; 514/560

(58) Field of Classification Search ............... 514/311, 514/549, 560
See application file for complete search history.

(56) References Cited

U.S. PATENT DOCUMENTS

| | | | | |
|---|---|---|---|---|
| 5,502,077 A | * | 3/1996 | Breivik et al. | 514/560 |
| 5,856,336 A | | 1/1999 | Fujikawa et al. | |
| 6,331,568 B1 | * | 12/2001 | Horrobin | 514/560 |
| 6,365,186 B1 | * | 4/2002 | Huval et al. | 424/486 |
| 6,777,552 B2 | | 8/2004 | Niddan-Heldesheim et al. | |
| 7,022,713 B2 | * | 4/2006 | Aoki et al. | 514/311 |
| 2002/0016312 A1 | | 2/2002 | Seed et al. | |
| 2003/0105028 A1 | | 6/2003 | Ghosal et al. | |
| 2004/0106556 A1 | * | 6/2004 | Zhu et al. | 514/12 |

OTHER PUBLICATIONS

Kiyoshi Mizuguchi, et al., "Ethyl all-cis-5,8,11,14,17-icosapentaenoate modifies the biochemical properties of rat very low-density lipoprotein," European Journal of Pharmacology, 235 (1993), pp. 221-227.

Kiyoshi Mizuguchi, et al., "The effect of eicosapentaenoic acid ethyl ester (EPA-E) on the metabolism of triglyceride," J. Jpn. Atheroscier. Soc., 18(5), 1990, pp. 536-537, with English translation.

N. Nakamura, et al., "Joint effects of HMG-CoA reductase inhibitors and eicosapentaenoic acids on serum lipid profile and plasma fatty acid concentrations in patients with hyperlipidemia," Int J Clin Lab Res (1999) 29, pp. 22-25.

Kiyoshi Mizuguchi, et al., "Mechanism of the lipid-lowering effect of ethyl all-cis-5,8,11,14,17-icosapentaenoate," European Journal of Pharmacology, 231 (1993), pp. 121-127.

Suzuki et al, Atherosclerosis 146 (1999) pp. 259-270.

Aoki et al, Arzneim.-Forsch./Drug Res. 47 (II), 8, (1997) pp. 904-909.

Norio Nakamura, et al., "HMG-CoA Reductase Inhibitors and the Metabolism of Polyunsaturated Fatty Acids-Joint Effects of Eicosapentaenoic Acid and HMG-CoA Reductase Inhibitors", Progress in Medicine, vol. 19, No. 8, Aug. 1999, pp. 105-111.

McKenney, Pharmacoltherapy, (2002), vol. 22, No. 7, pp. 853-863 (Abstract only Medicine Accession No. 2002380154).

"Pitavastatin, Itavastatin, Nisvastatin. Nk 104, Nks 104, P 872441", Drugs in R & D, ADIS International, vol. 3, No. 1, XP-008058974, 2002, pp. 58-60.

Arne Nordoey, et al., "n-3 Polyunsaturated Fatty Acids and Cardiovascular Diseases", Lipids, vol. 36, No. Suppl., XP-008060642, 2001, pp. S127-S129.

U. N. Das, "Essential fatty acids as possible mediators of the actions of statins", Prostaglandins Leukotrienes and Essential Fatty Acids, vol. 65, No. 1, XP-008060638, Jul. 2001, pp. 37-40.

A. Nordoey, et al., "Effects of Simvastatin and omega-3 fatty acids on plasma lipoproteins and lipid peroxidation in patients with combined hyperlipidaemia", Journal of Internal Medicine, vol. 243, No. 2, XP-002371430, Feb. 1998, pp. 163-170.

A. Nordoey, et al., Effects of atorvastatin and omega-3 fatty acids on LDL subfractions and postprandial hyperlipemia in patients with combined hyperlipemia, Nutrition Metabolism Cardiovascular Diseases, vol. 11, No. 1, XP-008060643, Feb. 2001, pp. 7-16.

T. Yano, et al., Life Sciences, vol. 61, No. 20, pp. 2007-2015 (1997).

J-B Hansen, et al., Arteriosclerosis and Thrombosis, vol. 13, No. 1, pp. 98-104 (1993).

Y. Saito, et al., Atherosclerosis, vol. 162, pp. 373-379 (2002).

\* cited by examiner

*Primary Examiner*—Raymond J Henley, III
(74) *Attorney, Agent, or Firm*—Oblon, Spivak, McClelland, Maier & Neustadt, L.L.P.

(57) ABSTRACT

A hypertriglyceridemia therapeutic agent made up of a synergistically effective blood-triglyceride decreasing amount of a combination of a pitavastatin and eicosapentaenoic acid (EPA), or an ester thereof.

7 Claims, 1 Drawing Sheet

Mean value ± standard error
N=8, **p<0.01 Dunnett
EPA-E=Ethyl eicosapentaenoate

HYPERLIPEMIA THERAPEUTIC AGENT

CROSS REFERENCE TO A RELATED APPLICATION

The present application is a continuation of U.S. application Ser. No. 10/780,640, filed Feb. 19, 2004, now U.S. Pat. No. 7,022,713.

FIELD OF THE INVENTION

The present invention relates to a hyperlipemia therapeutic agent, specifically to a hyperlipemia therapeutic agent showing an excellent decreasing action on both of the cholesterol and triglyceride in blood.

BACKGROUND OF THE INVENTION

Hyperlipemia is a symptom in which the lipoprotein in blood becomes abnormally excessive, and which is also strongly associated with diseases, such as arteriosclerosis and myocardial infarction, so its treatment is considered important.

Various medicines are used for the treatment of hyperlipemia, and HMG-COA reductase inhibitors such as pravastatin, simvastatin, fluvastatin and atorvastatin are mainly used as therapeutic agents therefor. It is known that pitavastatins have a strong HMG-CoA reductase inhibiting action and are useful as a blood cholesterol-reducing agent (Japanese Patent No. 2569746, U.S. Pat. No. 5,856,336 and European Patent No. 304063).

The main components of blood lipoprotein are cholesterol and triglyceride, and the blood cholesterol level of hyperlipemic patients not only increases, but is also accompanied with an increase in triglyceride in many cases. When an HMG-CoA reductase inhibitor is administered to hyperlipemic patients, blood cholesterol is sufficiently lowered, but triglyceride is not sufficiently lowered. Besides, there is a method by which hyperlipemic patients suffering from a high level of the cholesterol and triglyceride in blood are treated by increasing an administering dose of the HMG-CoA reductase inhibitor for the purpose of lowering both of cholesterol and triglyceride. However, this method is problematic over the safety issues and therefore is not recommended.

On the other hand, eicosapentaenoic acid (EPA) is a long-chain essential fatty acid contained primarily in fish oil, and this acid is reported to serve as an inhibition in absorption of triglyceride from an intestinal tract, an inhibition in biosynthesis in a liver, a reduction in blood triglyceride by enhancing a plasma lipoprotein lipase activity (Mizuguchi, K. et al.: Eur. J. Pharmacol. 235, 221 to 227, 1993, Mizuguchi, K. et al.: Arteriosclerosis 18 (5), 536, 1990), an inhibition in synthesis of liver cholesterol and a reduction in blood total cholesterol by an acceleration in excretion of cholesterol into bile (Mizuguchi, K. et al.: Eur. J. Pharmacol. 231, 121 to 127, 1993).

SUMMARY OF THE INVENTION

In light of such existing situations, the present inventor conducted intensive investigations and came to the conclusion that when used in combination with eicosapentaenoic acid or an ester derivative thereof, pitavastatins, among many HMG-CoA reductase inhibitors, provides an excellent effect of lowering both of the cholesterol and triglyceride in blood and is useful for treatment of hyperlipemia. Thus the present invention was completed.

Accordingly, the present invention provides a hyperlipemia therapeutic agent comprising pitavastatins and eicosapentaenoic acid or an ester derivative thereof as effective ingredients.

Also, the present invention provides a composition for treatment of hyperlipemia comprising pitavastatins, eicosapentaenoic acid or an ester derivative thereof and a pharmaceutically allowable carrier.

Further, the present invention provides a method for treating hyperlipemia characterized by administering pitavastatins and eicosapentaenoic acid or an ester derivative thereof.

The hyperlipemia therapeutic agent of the present invention has an excellent effect of lowering the cholesterol and triglyceride in blood and is useful for treatment of type IIb and type IV hyperlipemias.

DETAILED DESCRIPTION OF THE INVENTION

Figure 1:
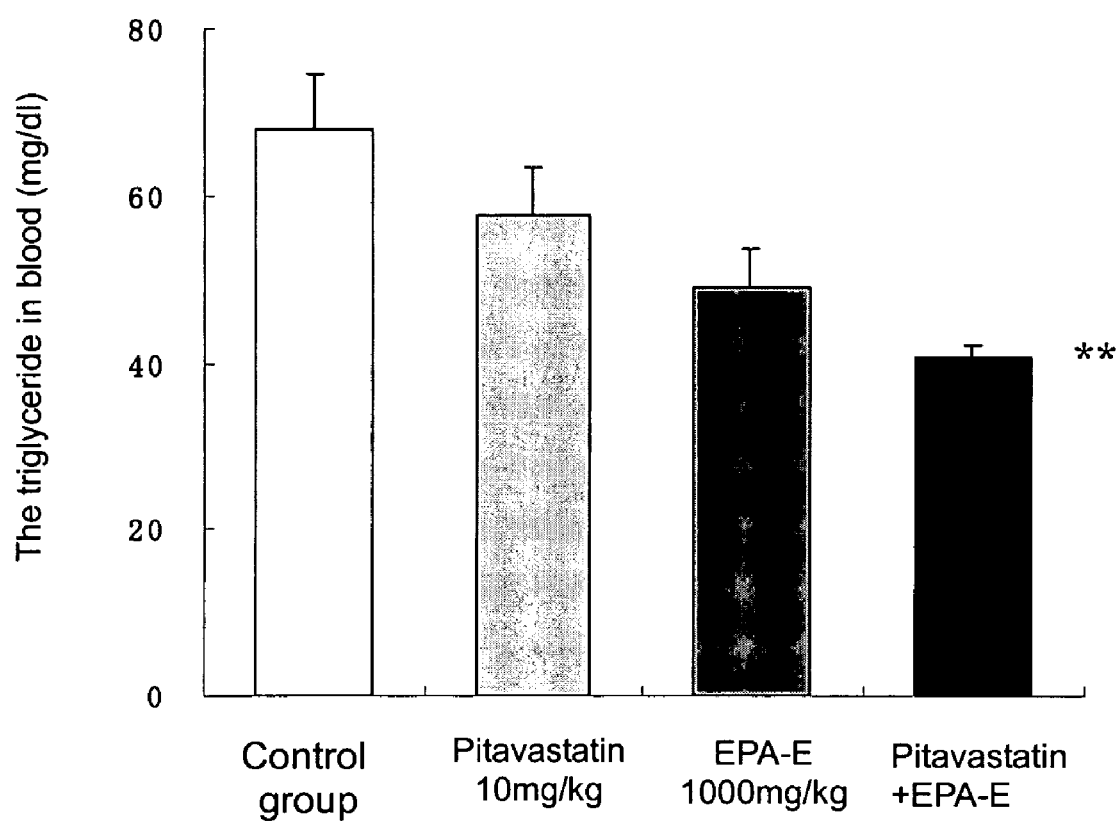
FIG. 1 is a drawing showing an effect of lowering the triglyceride in blood by administering ethyl eicosapentaenoate (EPA-E) in combination with pitavastatin calcium.

Pitavastatins used in the present invention include the compound pitavastatin ((3R,5S,6E)-7-[2-cyclopropyl-4-(4-fluorophenyl)3-quinolyl]-3,5-dihyroxy-6-heptenoic acid: Japanese Patent No. 2569746, U.S. Pat. No. 5,856,336 and European Patent No. 304063), lactone ring-forming substances thereof and salts of pitavastatin, and the salts of pitavastatin include pitavastatin sodium and pitavastatin calcium. Further, they include hydrates thereof and solvates thereof with solvents which are allowable as medicines. Pitavastatin calcium is the most preferred of the pitavastatins.

Pitavastatins can be produced by a method described in Japanese Patent No. 2569746, U.S. Pat. No. 5,856,336 and European Patent No. 304063.

Eicosapentaenoic acid in the present invention means all-cis-5,8,11,14,17-eicosapentaenoic acid and can readily be obtained by hydrolyzing natural glycerin esters obtained from fish oil and the others to remove glycerin parts thereof, and commercial products can be used as well. Further, above eicosapentaenoic acid may form salts with, for example, sodium and calcium.

Glycerin ester and lower alkyl esters can be given as the ester derivatives of eicosapentaenoic acid. Capable of being given as the lower alkyl esters are, for example, methyl ester, ethyl ester, propyl ester, isopropyl ester, n-butyl ester, isobutyl ester and t-butyl ester, and they are preferably methyl ester, ethyl ester and propyl ester, particularly preferably ethyl ester.

The glycerin ester can readily be extracted, as described above, from natural resources in the form of the natural glycerin ester. On the other hand, the lower alkyl esters can easily be produced by subjecting eicosapentaenoic acid to dehydration condensation with aliphatic lower alcohols.

A purity of the eicosapentaenoic acid and ester derivatives thereof described above shall not specifically be restricted, and the products having a high purity are preferred from the viewpoint that the dose can be reduced.

Pitavastatins (A) and eicosapentaenoic acid or the ester derivative thereof (B) are preferably contained in the hyperlipemia therapeutic agent of the present invention in a mass ratio of A:B=1:1 to 1 to 5000, further preferably 1:10 to 1:2000 in terms of an effect of lowering the cholesterol and triglyceride in blood, particularly an effect of lowering triglyceride.

The hyperlipemia therapeutic agent of the present invention in which pitavastatins are used in combination with eicosapentaenoic acid or the ester derivative thereof has, as shown in examples described later, an action able to strongly lower the triglyceride in blood in a rat, as compared with the case in which pitavastatin calcium alone is administered independently. Accordingly, the hyperlipemia therapeutic agent of the present invention is effective for treatment of hyperlipemia, especially for treatment of type IIB and type IV hyperlipemias in which both of cholesterol and triglyceride in blood show high values.

The hyperlipemia therapeutic agent of the present invention can be produced according to a conventional method by suitably mixing, in addition to the effective ingredients, with an excipient which is allowed according to the preparation form thereof, a decay agent, a binder, a slipping agent, a diluent, a buffer, an isotonizing agent, an antiseptic agent, a lubricant, an emulsifier, a dispersant, a stabilizing agent and a dissolution aid, diluting or dissolving them. Eicosapentaenoic acid or the ester derivative thereof is liable to be oxidized, and therefore an antioxidant such as, for example, BHA, BHT and tocopherol can be added if necessary.

In respect to the formulation of the hyperlipemia therapeutic agent of the present invention, the pharmaceutical preparations having various formulations can be use, and they can be, for example, a powder, a granule, a dry syrup, a tablet, a capsule and a parenteral solution.

The use form of the hyperlipemia therapeutic agent of the present invention shall not specifically be restricted, and both drugs may be administered at the same time or may be separately administered leaving an interval. That is, pitavastatins and eicosapentaenoic acid or the ester derivative thereof may be mixed with a diluent and an excipient which are pharmacologically allowable to form a single pharmaceutical preparation or pharmaceutical preparations may be separately produced from both drugs and used in the form of a set. When the pharmaceutical preparations are separately produced from both drugs, both pharmaceutical preparations may not have the same formulation.

A dose of the hyperlipemia therapeutic agent of the present invention is suitably selected according to the symptoms. Pitavastatins are administered in a dose of 0.1 to 100 mg, preferably 1 to 50 mg and more preferably 1 to 20 mg a day, and eicosapentaenoic acid or the ester derivative thereof is administered in a dose of 500 to 100000 mg, preferably 1000 to 60000 mg a day. They may be administered once a day or may be administered dividing into twice or more.

The present invention shall more specifically be explained below with reference to examples, but the present invention shall not be restricted to these examples.

EXAMPLES

An effect thereof on the blood triglyceride observed when ethyl eicosapentaenoate (EPA-E) and pitavastatin calcium were administered was measured according to the following method.

1. Tested Animal and Breeding Environment

Male Wistar rats aged 6 weeks (Japan Medical Science Experimental Animal Co., Ltd.) were tested. They were fed in a room maintained in a bright and dark cycle (bright duration by a room light: 7:00 a.m. to 7:00 p.m.) at a temperature of 23±3° C. and a humidity of 55±15% through an experimental duration and allowed to freely take a chow (CE-2; Nippon Clear Co., Ltd.) and city water.

2. Drug Preparation

Pitavastatin calcium was suspended in a 0.5 mass % aqueous solution of sodium carboxymethyl cellulose (Iwai Kagaku Yakuhin Co., Ltd.) and controlled so that a dose was 2 ml/kg. Pitavastatin calcium contained 9.43 mass % of water, and therefore an amount as 1.1 mass time much as the dose was weighed to correct the practical dose. The suspension was refrigerated (4° C.) in a shaded bottle, and it was prepared every 7 days. EPA-E was taken from Epadel capsule (Dainippon Seiyaku Co., Ltd.) in use, suspended in refined water and controlled so that a dose was 2 ml/kg.

3. Test Method

Thirty two rats were divided into the following four groups (eight examples per group), that is, a control group, a pitavastatin calcium alone (10 mg/kg) group, an EPA-E alone (1000 mg/kg) group and a pitavastatin calcium (10 mg/kg) and EPA-E (1000 mg/kg) combined use group so that total cholesterol and triglyceride in blood were equalized. Both drugs were orally administered once a day (4:00 p.m.) for 21 days, and a sodium carboxymethyl cellulose 0.5 mass % aqueous solution 1 ml/kg was orally administered to the control group. In all groups, blood was taken after fasting for 18 hours since the final administration to measure a triglyceride concentration in blood.

4. Statistical Analysis and Data Processing Method

The differences of multiple groups between the control group and the drug-administered groups were analyzed using Dunnett's multiple comparison test, preceded by Bartlett's analysis of variance. P values less than 5% were considered statistically significant.

As shown in FIG. 1, the triglyceride in blood tended to be lowered in the pitavastatin calcium alone group and the EPA-E alone group. In the meantime, blood triglyceride was lowered to a large extent in the both drugs combined use group as compared with the pitavastatin calcium alone group, and a synergistic effect was confirmed (K. Takagi et al.: Pharmacology, 1987, Nanzan Do)(p<0.01).

What is claimed is:

1. A hypertriglyceridemia therapeutic agent comprising a synergistically effective blood-triglyceride decreasing amount of a combination of a pitavastatin and eicosapentaenoic acid (EPA) or an ester thereof.

2. The therapeutic agent according to claim 1, wherein the pitavastatin is pitavastatin calcium and the eciosapentaenoic acid (EPA) or ester thereof is ethyl eicosapentaenoate.

3. The therapeutic agent of claim 1, wherein the eicosapentaenoic acid or an ester thereof is selected from the group consisting of the calcium salt of EPA, the sodium salt of EPA, the n-butyl ester of EPA, the isobutyl ester of EPA, the t-butyl ester of EPA, the glycerin ester of EPA, the ethyl ester of EPA, and combinations thereof.

4. The therapeutic agent of claim 1, wherein the eicosapentaenoic acid or an ester thereof is selected from the group consisting of the calcium salt of EPA, the sodium salt of EPA, the n-butyl ester of EPA, the isobutyl ester of EPA, the t-butyl ester of EPA, the glycerin ester of EPA, and combinations thereof.

5. The therapeutic agent of claim 1, wherein the ratio of pitavastatin to EPA or an ester thereof is 1:100.

6. The therapeutic composition of claim 5, comprising 1 to 20 mg of pitavastatin.

7. The therapeutic composition of claim 1, wherein the ratio of pitavastatin to EPA or an ester thereof is 1:100 to 1:2000.

* * * * *